United States Patent
Thappa

(10) Patent No.: US 6,939,326 B1
(45) Date of Patent: Sep. 6, 2005

(54) CLOSED-END INFUSION CATHETER WITH AN INTRODUCER AND A METHOD FOR USING THE SAME

(76) Inventor: Vivek Thappa, 3703 Sherbrook Rd., Rockford, IL (US) 61114

( * ) Notice: Subject to any disclaimer, the term of this patent is extended or adjusted under 35 U.S.C. 154(b) by 173 days.

(21) Appl. No.: 09/695,116

(22) Filed: Oct. 24, 2000

(51) Int. Cl.[7] .................. A61M 25/00; A61M 5/32; A61M 5/178
(52) U.S. Cl. .................. 604/164.01; 604/272; 604/179; 604/177; 604/164.12; 604/264
(58) Field of Search .......................... 606/200, 191, 606/170, 159, 213; 604/104, 164.12, 523, 604/272, 110, 265, 194, 170.01, 528, 510, 604/264, 175, 28, 93.01, 167.06, 8–44, 529, 604/177, 540, 541, 162, 506, 164.01; 600/114, 600/120, 235, 204, 185, 131

(56) References Cited

U.S. PATENT DOCUMENTS

| | | | |
|---|---|---|---|
| 3,827,434 A | 8/1974 | Thompson et al. | |
| 4,147,165 A | 4/1979 | Tauschinski | |
| 4,299,228 A | 11/1981 | Peters | |
| 4,392,855 A | 7/1983 | Oreopoulos et al. | |
| 4,491,126 A | 1/1985 | Cullor | |
| 4,529,399 A | 7/1985 | Groshong et al. | |
| 4,545,373 A | 10/1985 | Christoudias | |
| 5,098,413 A | 3/1992 | Trudell et al. | |
| 5,141,499 A | 8/1992 | Zappacosta | |
| 5,360,414 A * | 11/1994 | Yarger | 604/264 |
| 5,735,829 A | 4/1998 | Cherian | |
| 5,759,150 A * | 6/1998 | Konou et al. | 600/114 |
| 5,800,409 A | 9/1998 | Bruce | |
| 5,830,229 A | 11/1998 | Konya et al. | |
| 5,910,134 A | 6/1999 | Fussman | |
| 6,059,802 A * | 5/2000 | Ginn | 606/114 |

FOREIGN PATENT DOCUMENTS

WO          WO 93/13820          7/1993

* cited by examiner

Primary Examiner—Nicholas D. Lucchesi
Assistant Examiner—Roz Maiorino
(74) Attorney, Agent, or Firm—Patents & TMS, P.C.

(57) ABSTRACT

An introducer for a catheter and a closed-end infusion catheter are provided. The catheter may be porous or may have a number of holes in which to infuse anesthetics into a body area of a patient. The introducer allows for introducing and proper placement of the catheter in the body of the patient. In addition, a method for using the introducer to place the catheter in the body of the patient is provided. The introducer may pierce the skin of the patient and may be inserted through the subcutaneous layer to an exit site. After a portion of the introducer protrudes through the exit site, the catheter may be attached to the introducer. The introducer may be pulled into the body, through the subcutaneous layer and out of the body at the original entry site. The introducer may then be removed, and the catheter may be pulled into place and sutured to the skin.

25 Claims, 6 Drawing Sheets

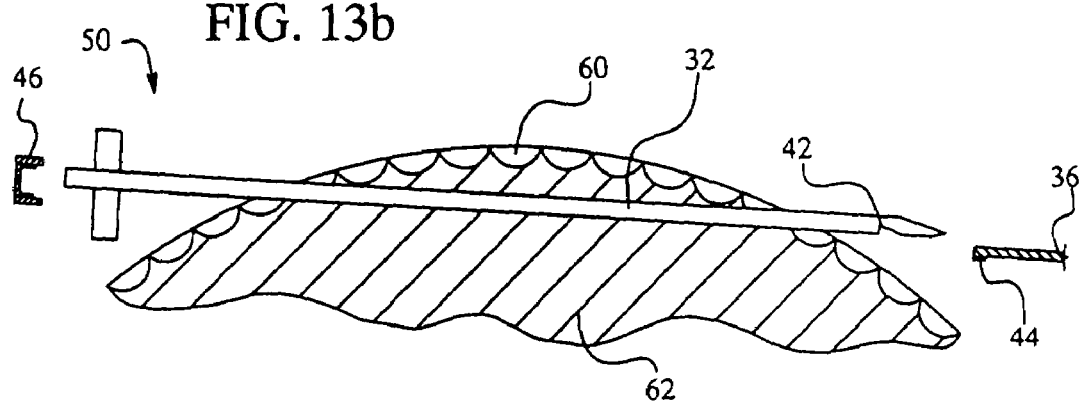

CLOSED-END INFUSION CATHETER WITH AN INTRODUCER AND A METHOD FOR USING THE SAME

BACKGROUND OF THE INVENTION

The present invention generally relates to a closed-end infusion catheter. The closed-end infusion catheter (hereinafter "catheter") may be porous having holes in which to infuse a body area of the patient with an anesthetic. An introducer allows for introducing the closed-end infusion catheter into the body and proper placement of the catheter. In addition, the present invention provides a method for placing a catheter in a body of a patient.

It is, of course, generally known to use a catheter to apply anesthetic locally to different areas of the body. Various types of catheters as well as methods for inserting and securing catheters are also known. For example, in U.S. Pat. No. 5,735,829 to Cherian, a catheter is inserted during thoracic surgery by a surgeon. The catheter disclosed by Cherian has a plurality of spaced ports such that anesthetic is delivered directly to the intercostal nerves. In U.S. Pat. No. 5,141,499 to Zappacosta, a peritoneal dialysis catheter is disclosed. The peritoneal dialysis catheter disclosed in Zappacosta carries one to two porous cuffs to facilitate permanent securance of the catheter to the abdominal wall. The catheter has a plurality of flow ports, and its end may be open as well for additional flow communication.

However, use of such known catheters often results in a significant problem with the risk of post-operative infection and discomfort to the patient.

A need, therefore, exists for a device, an introducer and a method designed to quickly and to efficiently distribute anesthetic to a patient by use of a catheter.

SUMMARY OF THE INVENTION

The present invention provides an introducer for a catheter and a closed-end infusion catheter (hereinafter "catheter"). The catheter may be porous with a number of holes in which to infuse an anesthetic into a body area of the patient. The introducer allows for introducing and proper placement of the catheter. In addition, the present invention provides a method for using the introducer to properly place the catheter in the body of the patient.

To this end, in an embodiment of the present invention, a catheter introducing device for placing a catheter within a body has a cylindrical body defining a cross with a length defined between a pointed end and a flat end. The catheter introducing device also has a first part and a second part both having a uniform width and a length defined between the pointed end and the flat end. The first part defines a cross and the first part and the second part together define the cylindrical body.

In an embodiment, a locking mechanism is located at the flat end of the cylindrical body. The first part and the removable second part are locked together.

In an embodiment, the pointed end of the cylindrical body gradually tapers to a cylindrical portion.

In an embodiment, the catheter introducing device has sufficient structural strength to penetrate through skin and into a subcutaneous layer of a body.

In an embodiment, a recessed portion is provided along the length of the first part and a protruding element defined in shape by a right angle is located along the recessed portion of the first part.

In an embodiment, a protrusion along the length of the removable second part of the cylindrical body is provided wherein the recessed portion along the length of the first part may readily accept the protrusion along the length of the removable second part.

In another embodiment of the present invention, the catheter introducing device for placing a catheter within a body has a cylinder having a length defined between a pointed end and a bottom end. The catheter introducing device also has a leg attached perpendicularly to the bottom end of the cylinder. The catheter introducing device further has a first hole located a distance from the pointed end of the cylinder and a second hole located on the leg of the cylinder. A thread is connected to the cylinder from the second hole to the first hole.

In an embodiment, a groove is cut into the cylinder and has a length defined between the first hole and the pointed end.

In an embodiment, a locking mechanism is located on the leg of the cylindrical body.

In an embodiment, the pointed end of the cylinder gradually tapers to a cylindrical portion.

In an embodiment, the cylinder has sufficient structural strength to penetrate through skin and into a subcutaneous layer of a body.

In another embodiment of the present invention, a catheter for infusing a local anesthetic has a flexible hollow body defining a length between a pointed end and a bottom end. The pointed end is closed and tapers to a cylindrical tube. The catheter further has a diameter defined by the cylindrical tube with a width defined by the bottom end of the flexible body. The width is greater than the diameter. The catheter also has a locking mechanism located on the bottom end of the flexible body, as well as a first and second notch located a distance from where the pointed end meets the cylindrical tube and a distance from the bottom end, respectively.

In an embodiment, the catheter is a flexible hollow body and is constructed of a porous material. The flexible hollow body may have a plurality of holes.

In another embodiment of the present invention, a method for introducing a catheter into the skin and the subcutaneous layer in a body of a patient is provided. The method comprises the steps of: providing an instrument; piercing the skin and the subcutaneous layer of the body with the instrument; pushing the instrument through the subcutaneous layer to an exit site outside of the body; attaching a catheter to the instrument; pulling the instrument and the catheter back into the subcutaneous layer and the entry site; removing the instrument from the catheter; and pulling the catheter back into the subcutaneous layer.

In an embodiment, the catheter is prevented from slipping into the body and from slipping out of the body.

In an embodiment, the catheter is sutured to the skin of the body.

In an embodiment, the catheter is attached to the instrument by placing a catheter on the instrument.

In an embodiment, the catheter is secured to an instrument with a thread.

In an embodiment, the catheter is secured to an instrument by fitting the catheter to a notch on the instrument.

It is, therefore, an advantage of the present invention to provide a a catheter introducing device for placing a catheter within a body.

Another advantage of the present invention is to provide a catheter for infusing a local anesthetic.

And, another advantage of the present invention is to provide a catheter having a flexible hollow body constructed of a porous material or having a plurality of holes.

A further advantage of the present invention is to provide a locking mechanism located at the end of the catheter.

A still further advantage of the present invention is to provide a catheter introducing device that has sufficient structural strength to penetrate through skin and into a subcutaneous layer of a body.

Another advantage of the present invention is to provide a catheter introducing device with a groove cut into the introducing device to accommodate a catheter.

A further advantage of the present invention is to secure the catheter to an instrument with a thread.

A still further advantage of the present invention is to secure the catheter to an instrument by fitting the catheter to a notch on the instrument.

Moreover, an advantage of the present invention is to provide a method for introducing a catheter into the skin and the subcutaneous layer in a body of a patient.

And, another advantage of the present invention is to prevent a catheter from slipping and to suture the catheter to the skin of the body.

Additional features and advantages of the present invention are described in, and will be apparent from, the detailed description of the presently preferred embodiments and from the drawings.

BRIEF DESCRIPTION OF THE DRAWINGS

FIGS. 13a and 13b are cross-sectional views of an embodiment of a method releasing the locking mechanism of one type of introducer.

DETAILED DESCRIPTION OF THE PRESENTLY

Preferred Embodiments

The present invention generally relates to an introducer for a a closed-end infusion catheter. The closed-end infusion catheter (hereinafter "catheter") preferably is porous with a number of holes in which to infuse anesthetics into a body area of a patient. The introducer allows for introducing and proper placement of the catheter. In addition, the present invention provides a system and a method for using the introducer to properly place the catheter in a body of a patient.

Figure 1:
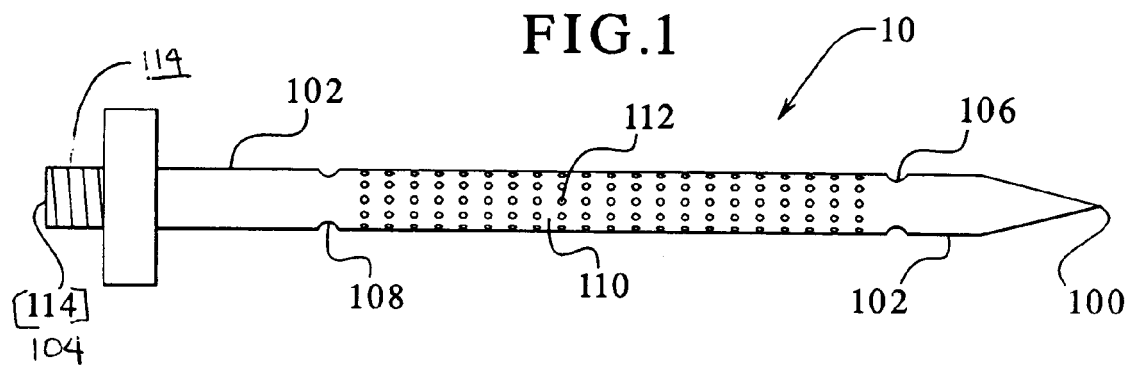
FIG. 1 is a side view of an embodiment of a catheter of the present invention.

Referring now to the drawings wherein like numerals refer to like parts, in FIG. 1, a closed-end infusion catheter 10 is generally illustrated. The catheter 10 is preferably constructed of a flexible material, such as for example, a flexible plastic. The catheter 10 preferably has a pointed end 100 and a bottom end 104. The pointed end 100 may taper to a cylindrical tube 102. The bottom end 104 of the cylindrical tube 102 preferably has a width greater than the diameter of the cylindrical tube 102. The catheter 10 preferably has a locking mechanism 114 located near the bottom end 104 of the cylindrical tube 102. A notch 106 may be located near the pointed end 100, and a second notch 108 may be located near the bottom end 104. The cylindrical tube 102 may be constructed of a porous material 110, or alternatively, with a plurality of holes 112 throughout its length. In an embodiment, the catheter 10 may be used, for example, during cardiac surgery to deliver a local anesthetic directly to nerves of a sternum of a patient. Or, for example, the catheter 10 may be used by a paramedic to deliver local anesthetic to the knee of an injured person prior to transporting the person to a hospital.

Figure 2:
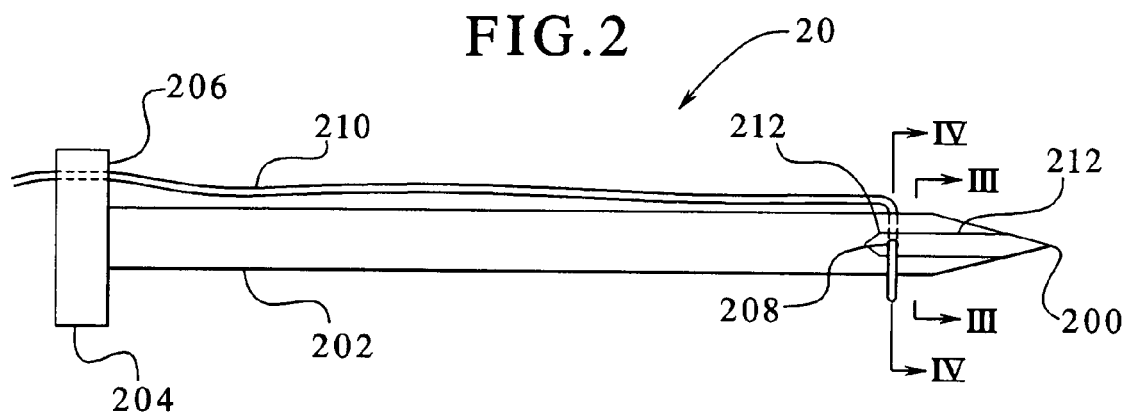
FIG. 2 is a plan view illustration of an embodiment of an introducer of the present invention.

Referring now to FIG. 2, an introducer 20 is illustrated. The introducer 20 may have a cylindrical rod 202 defined by a base 204 and a pointed tip 200. The base 204 is preferably wider than the diameter of the cylindrical rod 202. The pointed tip 200 tapers to the cylindrical rod 202. The introducer 20 is preferably constructed of a material of sufficient structural strength to pierce skin, such as, for example, steel or plastic. The introducer 20 may have a first hole 208 placed in a groove 212 in the cylindrical rod 202 at a distance from the pointed tip 200 of the introducer 20. The introducer 20 has a second hole 206 at the base 204. A loop 210 may extend through the first hole 208 and the second hole 206 at either end of the introducer 20. Preferably, the loop 210 is a monofilament nylon thread. The loop 210 may enter one side of the introducer 10 and may exit in the groove 212 placed into the side of the pointed tip 200 of the introducer 20.

Figure 3:
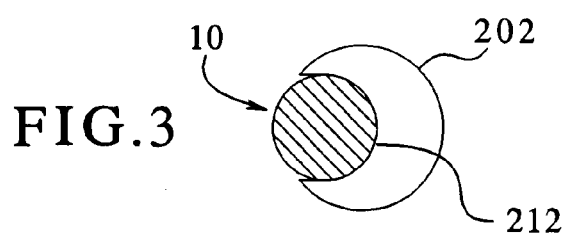
FIG. 3 is a cross-sectional view of an embodiment of a catheter taken along lines III—III of FIG. 2 of the present invention.
Figure 4:
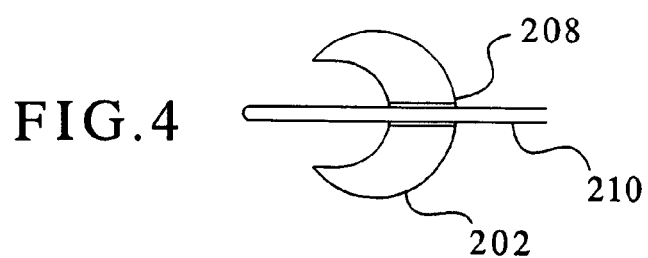
FIG. 4 is a cross-sectional view of an embodiment of a catheter taken along lines IV—IV of FIG. 2 of the present invention.

FIG. 3 illustrates a cross-sectional view of the catheter 10 placed on the introducer 20 at the groove 212 in the cylindrical rod 202. FIG. 4 illustrates a cross-sectional view of the introducer 20 at the first hole 208 in the groove 212 in the cylindrical rod 202.

Figure 17:
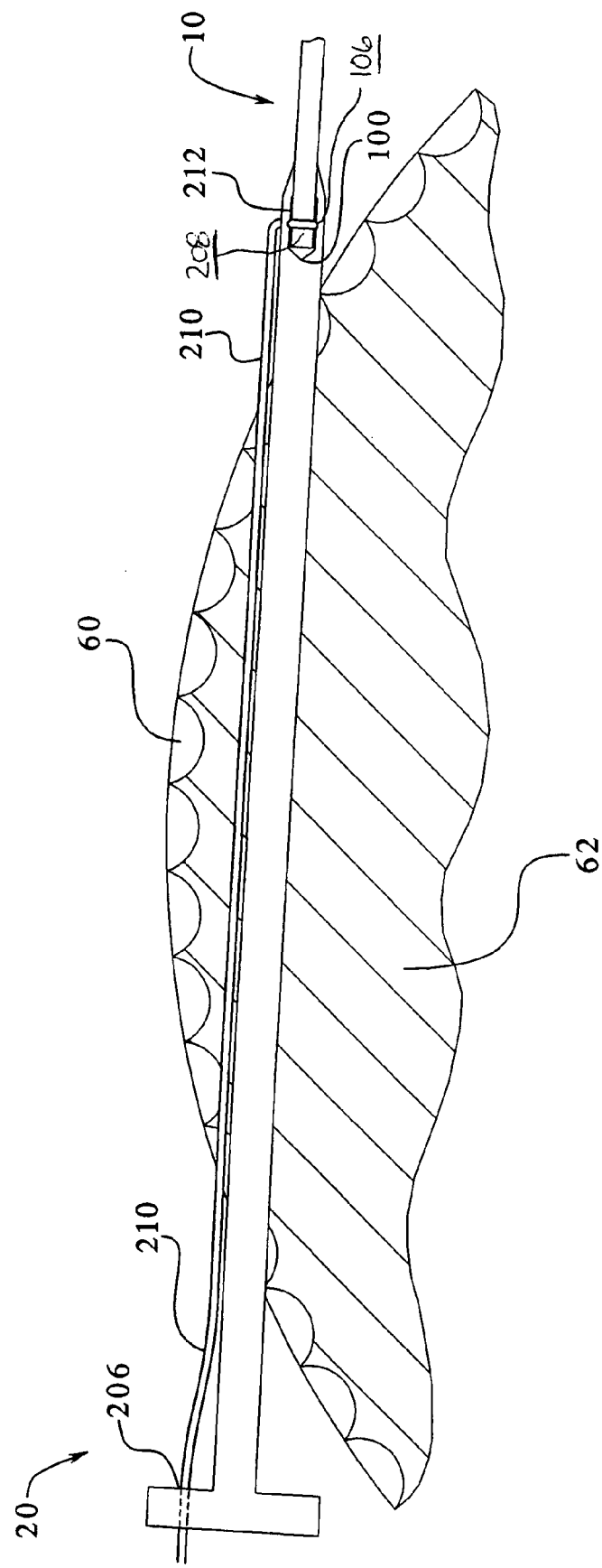
FIG. 17 is a cross-sectional view of an embodiment of a method of attaching a catheter to an introducer.

In a preferred embodiment, the groove 212 accepts the catheter 10 during insertion as shown in FIG. 17.

Figure 5:
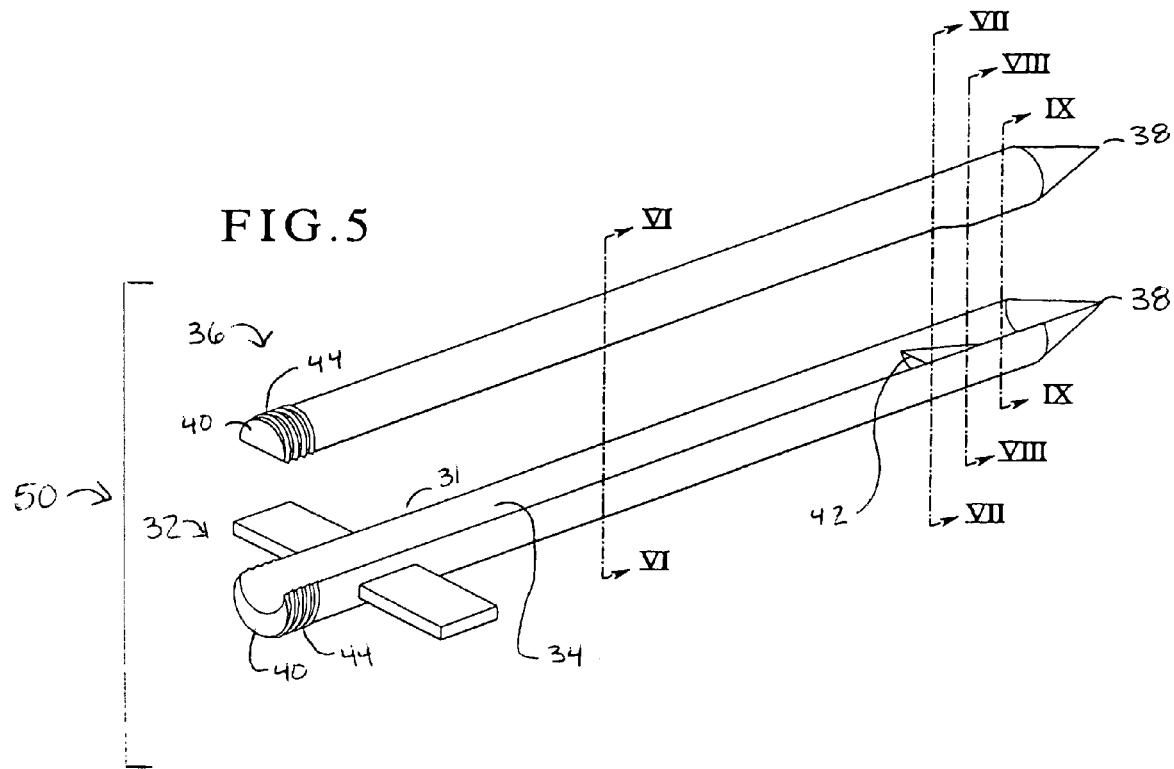
FIG. 5 is a plan view of an embodiment of an introducer of the present invention.
Figure 6:
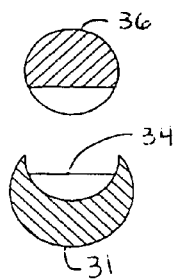
FIG. 6 is a cross-sectional view of an embodiment of a catheter taken along lines VI—VI of FIG. 5 of the present invention.
Figure 7:
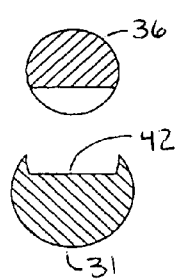
FIG. 7 is a cross-sectional view of an embodiment of a catheter taken along lines VII—VII of FIG. 5 of the present invention.
Figure 8:
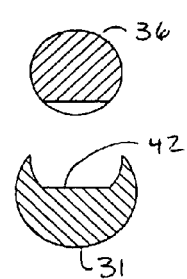
FIG. 8 is a cross-sectional view of an embodiment of a catheter taken along lines VIII—VIII of FIG. 5 of the present invention.
Figure 9:
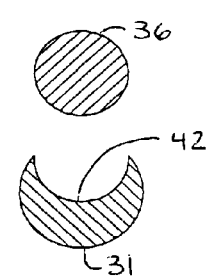
FIG. 9 is a cross-sectional view of an embodiment of a catheter taken along lines IX—IX of FIG. 5 of the present invention.

Alternatively, an introducer 50 may be designed as generally illustrated in FIG. 5. The introducer 50 may be constructed of two elements that form a cylindrical cross. The introducer 50 may have a pointed end 38 and a blunt end 40. The first element 32 of the introducer is preferably a cross-shaped cylindrical rod 31 with a circular cut 34 from the blunt end 40 to a right angle notch 42. The second element 36 may fit into the circular cut 34 of the first element 32 of the introducer 50. The blunt end 40 may have grooves 44 on both the first element 32 and the second element 36. As a result, the first element 32 and the second element 36 together form a locking mechanism. Cross-sections taken along lines VI—VI, VII—VII, VIII—VIII and IX—IX are shown in FIGS. 6–9, respectively. FIG. 6 generally illustrates a cross-section of the introducer 50 taken along its length. FIGS. 7–9 generally illustrate the right angle notch 42 located within the circular cut 34 of the first element 32 and the corresponding cross-section on the second element 36.

Figure 10:
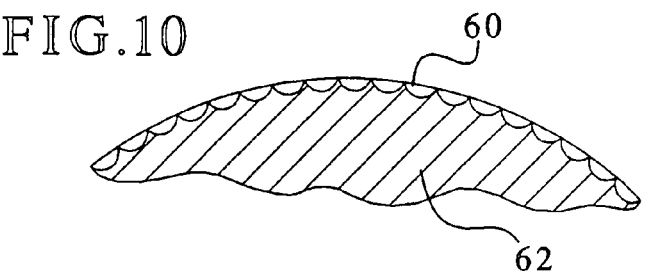
FIG. 10 is a cross-sectional view of skin and subcutaneous tissue.
Figure 11:
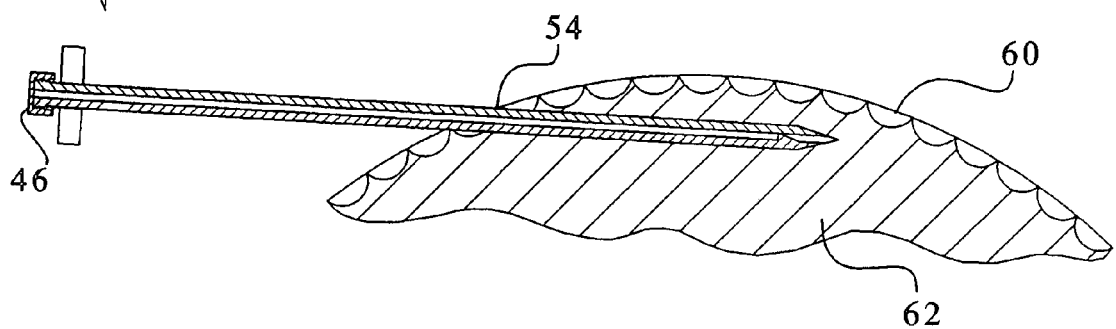
FIG. 11 is a cross-sectional view of an embodiment of a method of insertion of an introducer into the body of a patient.
Figure 12:
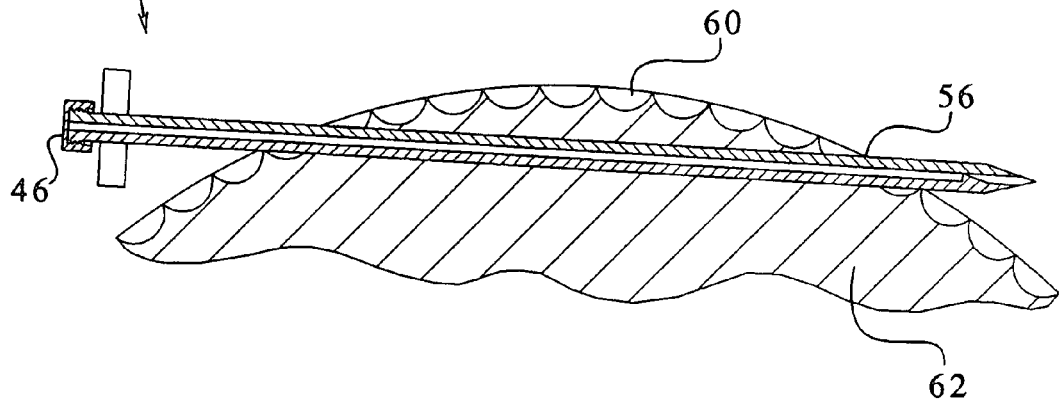
FIG. 12 is a cross-sectional view of an embodiment of a method of the introducer in the body of a patient and at the exit site of the body of the patient.
Figure 13A:
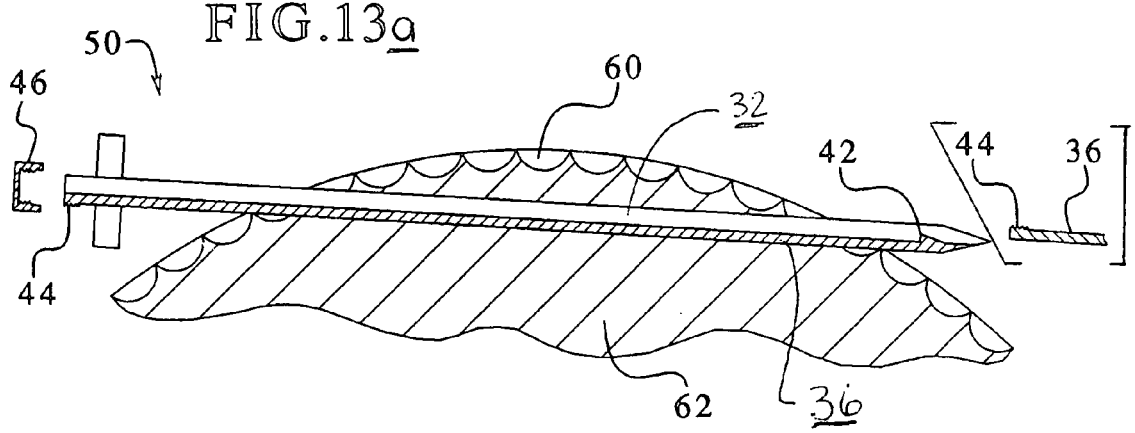

In an embodiment of the present invention, the introducer 50 may be used to introduce the catheter 10 into a body. For example, FIG. 10 illustrates skin 60 and the subcutaneous tissue 62 located under the skin 60 of a human being or patient. As shown in FIG. 11, the introducer 50 may be pushed into the skin 60 at an entry site 54 and to the subcutaneous tissue 62. FIG. 12 generally illustrates the introducer 50 in the subcutaneous tissue 62 and proceeding to an exit site 56. After the introducer 50 protrudes outside the exit site 56, the second element 36 of the introducer 50 may be removed as shown in FIGS. 13a and 13b. A locking mechanism is formed by the grooves 44 and a cap 46. The cap 46 is removed from the blunt end 40 of the introducer 50, thereby releasing the lock between the first element 32 from the second element 36. The second element 36 of the introducer 50 may be removed.

Figure 14:
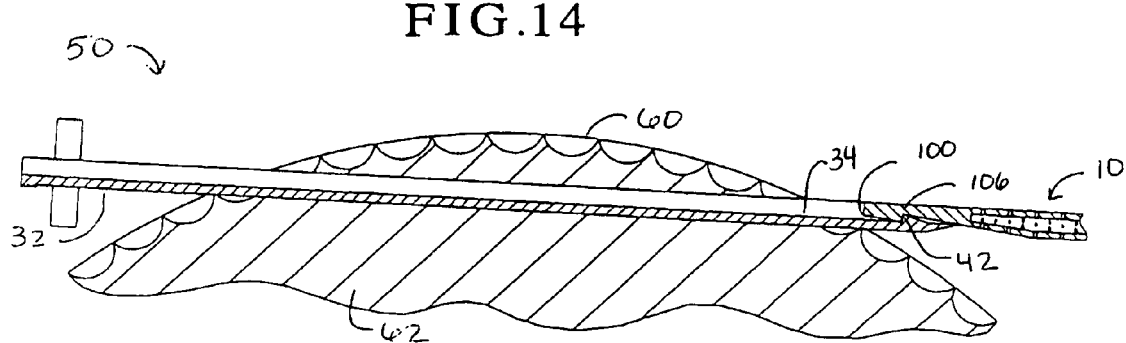
FIG. 14 is a cross-sectional view of an embodiment of a method of one type of introducer accepting a catheter.

As shown in FIG. 14, the catheter 10 may be attached to the first element 32 of the introducer 50. The pointed end 100 of the catheter 10 may be placed in the circular cut 34 of the first element 32 of the introducer 50. The catheter 10 may be secured by placing the notch 106 of the catheter 10 at the right angle notch 42 of the first element 32. As a result, the catheter 10 and the first element 32 fit together, and the catheter 10 may be kept from slipping away from the introducer 50 while located in the subcutaneous tissue 62 of the body.

Alternatively, as shown in FIG. 17, when using the introducer 20, the catheter 10 may be attached by placing the pointed end 100 of the catheter 10 on the groove 212 of the introducer 20. The notch 106 in the catheter may be aligned with the first hole 208 in the introducer 20. The loop 210 may then be secured around the catheter 10 at the notch 106 of the catheter 10.

Figure 15:
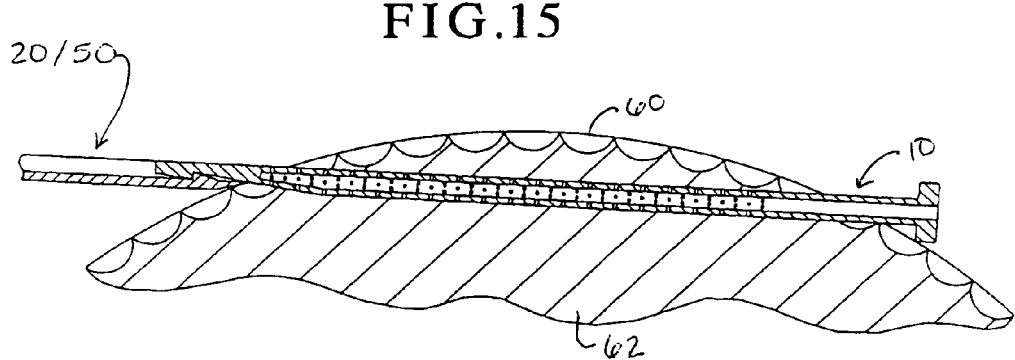
FIG. 15 is a cross-sectional view of an embodiment of a method of the removal of the introducer from the body of the patient.
Figure 16:
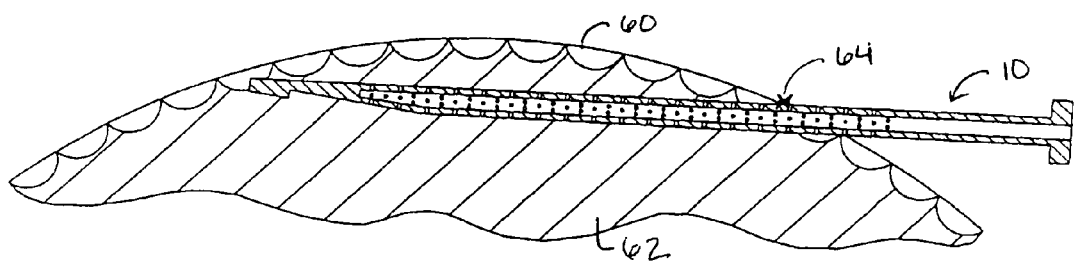
FIG. 16 is cross-sectional view of an embodiment of the catheter properly placed in the body of the patient.

As shown in FIG. 15, after the catheter 10 is attached to the introducer 20 or 50, the introducer 20 or 50 may be pulled back into the subcutaneous tissue 62 and back through the entry site 54. The introducer 20 or 50 may then be removed, and the catheter 10 may be pulled back into the subcutaneous tissue 62 to its desired location. The catheter 10 may then be secured in place with a suture 64 as shown in FIG. 16.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:
1. A catheter assembly for placing within a body, the catheter assembly comprising:
   a flexible hollow body having a length defined between a pointed end and a bottom end wherein the pointed end is closed and further wherein the flexible hollow body is a cylindrical tube having a diameter and further wherein the bottom end of the flexible body has a width greater than the diameter;
   a locking mechanism located on the bottom end of the flexible body;
   a first notch located on the flexible body at a distance from the pointed end;
   a second notch located on the flexible body at a distance from the bottom end; and
   a cylindrical body having a length defined between a pointed end and a blunt end wherein the cylindrical body is formed by a first element and a second element wherein the first element has a length defined between the pointed end and the blunt end wherein the first element has a uniform width between the pointed end and the blunt end and further wherein the first element is cross-shaped wherein the first element is removably attached to the second element and further wherein the pointed end of the flexible hollow body is removably attached to the first element of the cylindrical body wherein the first notch of the flexible hollow body secures to the pointed end of the first element.

2. The catheter assembly of claim 1 further comprising:
   a locking mechanism located at the blunt end of the cylindrical body wherein the first element and the second element are locked together.

3. The catheter assembly of claim 1 further comprising:
   a cylindrical portion of the cylindrical body wherein the pointed end of the cylindrical body gradually tapers to the cylindrical portion.

4. The catheter assembly of claim 1 wherein the cylindrical body has sufficient structural strength to penetrate through skin and into a subcutaneous layer of a body.

5. The catheter assembly of claim 1 further comprising:
   a recessed portion along the length of the first element; and
   a protruding element defined in shape by a right angle located along the recessed portion of the first element.

6. The catheter assembly of claim 5 further comprising:
   a protrusion along the length of the second element of the cylindrical body wherein the recessed portion along the length of the first element receives the protrusion along the length of the second element.

7. A catheter assembly for placing within a body, the catheter assembly comprising:
   a flexible hollow body defining a length between a top end and a bottom end wherein the top end is closed and wherein the top end tapers to a cylindrical tube;
   a diameter defined by the cylindrical tube;
   a width defined by the bottom end of the flexible body wherein the width is greater than the diameter;
   a locking mechanism located on the bottom end of the flexible body;
   a first notch located a distance from a point at which the top end meets the cylindrical tube;
   a second notch located a distance from the bottom end;

a cylinder having a length defined between a pointed end and a second end wherein the top end of the flexible hollow body is removably attached to the pointed end of the cylinder;

a first hole located a distance from the pointed end of the cylinder;

a leg attached to the bottom end of the cylinder;

a second hole located on the leg of the cylinder; and a thread connected to the cylinder from the second hole to the first hole.

8. The catheter assembly of claim 7 further comprising:
a groove cut into the cylinder having a length defined between the first hole and the pointed end.

9. The catheter assembly of claim 7 further comprising:
a locking mechanism located on the leg of the cylindrical body.

10. The catheter assembly of claim 7 further comprising:
a cylindrical portion wherein the pointed end of the cylinder gradually tapers to the cylindrical portion.

11. The catheter assembly of claim 7 wherein the cylinder has sufficient structural strength to penetrate through skin and into a subcutaneous layer of a body.

12. A catheter for infusing a local anesthetic into tissue located under skin of a patient, the catheter comprising:
a flexible hollow body having a length defined between a pointed end and a bottom end wherein the pointed end is closed wherein the flexible hollow body is a cylindrical tube having a diameter wherein the bottom end of the flexible hollow body has a width greater than the diameter and further wherein the flexible hollow body has a plurality of holes defining passageways to deliver the local aesthetic to the tissue of the patient wherein the passageways extend from an interior of the flexible hollow body to an exterior of the flexible hollow body;
a locking mechanism located on the bottom end of the flexible body; and
a notch located on the flexible hollow body at a distance between the pointed end and the plurality of holes wherein the notch is pulled inward with respect to the skin of the patient to place the flexible hollow body in the tissue of the patient and further wherein the pointed end and the bottom end of the flexible hollow body extend outward with respect to the skin of the patient.

13. The catheter of claim 12 wherein the flexible hollow body is constructed of a porous material.

14. A method for introducing a catheter into a body of a patient wherein the body includes skin and a subcutaneous layer, the method comprising the steps of:
providing a flexible hollow body defining a length between a top end and a bottom end and having a notch located a distance from the top end;
providing a second notch located a distance from the bottom end;
providing a first part having a length defined between a pointed end and a flat end;
providing a second part having a length defined between the pointed end and the flat end wherein the first part and the second part define a cylindrical body and further wherein the second part is removable;
providing a locking mechanism located at the flat end of the cylindrical body wherein the first part and the second part are locked together;
piercing the skin and the subcutaneous layer of the body with the pointed end of the cylindrical body;
pushing the cylindrical body through the subcutaneous layer wherein the cylindrical body is exposed outside an exit site of the body;
removing the second part of the cylindrical body;
attaching the notch of the flexible hollow body to the first part of the cylindrical body;
pulling the first part of the cylindrical body and the flexible hollow body into the subcutaneous layer and the entry site; and
removing the first part of the cylindrical body from the flexible hollow body and pulling the flexible hollow body into the subcutaneous layer.

15. The method of claim 14 further comprising the step of:
preventing the flexible hollow body from slipping.

16. The method of claim 14 further comprising the step of:
suturing the flexible hollow body to the skin of the body.

17. The method of claim 14 further comprising the step of:
attaching the flexible hollow body to the first part of the cylindrical body by placing the top end of the flexible hollow body on the first part of the cylindrical body.

18. The method of claim 14 further comprising the step of:
securing the flexible hollow body to the first part of the cylindrical body with a thread.

19. The method of claim 14 further comprising the step of:
securing the flexible hollow body to the first part of the cylindrical body by fitting the flexible hollow body to a notch on the first part of the cylindrical body.

20. The catheter assembly of claim 1 wherein the flexible hollow body is constructed of a porous material.

21. The catheter assembly of claim 1 wherein the flexible hollow body has a plurality of holes.

22. The catheter assembly of claim 7 wherein the flexible hollow body is constructed of a porous material.

23. The catheter assembly of claim 7 wherein the flexible hollow body has a plurality of holes.

24. The method of claim 14 wherein the flexible hollow body is constructed of a porous material.

25. The method of claim 14 wherein the flexible hollow body has a plurality of holes.

* * * * *